US00PP34341P2

(12) United States Plant Patent
Hansen

(10) Patent No.: US PP34,341 P2
(45) Date of Patent: Jun. 14, 2022

(54) ***HOSTA* PLANT NAMED 'ABOVE THE CLOUDS'**

(50) Latin Name: ***Hosta* hybrid (Tratt.)**
Varietal Denomination: Above the Clouds

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,985

(22) Filed: Jan. 10, 2022

(51) Int. Cl.
*A01H 5/02* (2018.01)
*A01H 6/12* (2018.01)

(52) U.S. Cl.
USPC ..... Plt./353

(58) Field of Classification Search
USPC ..... Plt./263.1, 353
See application file for complete search history.

*Primary Examiner* — Karen M Redden

(57) ABSTRACT

A new and distinct *Hosta* plant named 'Above the Clouds' producing medium mounds of highly-glaucous, bluish, nearly-rounded to broadly ovate leaves of strongly glaucous bluish color. The flowers are white with light lavender centers and pale lavender backs. Flowers are subtended by floral bracts of a closely matching color making the whole scape more effective. 'Above the Clouds' is useful in the landscape, as a container plant, a specimen or en masse.

2 Drawing Sheets

Botanical classification: *Hosta* hybrid (Tratt.).
Variety denomination: 'Above the Clouds'.

STATEMENT REGARDING PRIOR DISCLOSURES UNDER 37 CFR 1.77(B)(6)

*Hosta* 'Above the Clouds' was first introduced by the inventor as a non-enabling description in registration of the name in early 2021 with the International Cultivar Registration Authority for the genus *Hosta*. Other non-enabling disclosure include the website introduction by Walters Gardens, Inc. on Dec. 1, 2021. No plants of *Hosta* 'Above the Clouds' have been sold in this country or anywhere in the world, nor has any enabling disclosure of the new plant been made.

BACKGROUND AND ORIGIN OF THE PLANT

The present invention relates to a new and distinct *Hosta* plant, 'Above the Clouds' hereinafter also referred to as the new plant or by the cultivar name, 'Above the Clouds'. *Hosta* 'Above the Clouds' was hybridized by the inventor on Jul. 6, 2011 at a wholesale perennial nursery in Zeeland, Mich., USA. The female parent was 'Silver Moon' (not patented) and the male parent was a proprietary unnamed sport of 'Liberty' (not patented). 'Liberty' itself is U.S. Plant Pat. No. 12,531. The seeds from this cross were collected on Oct. 13, 2011 and a single seedling from this cross eventually produced the new plant. The new plant was assigned the breeder code 11-48-1 and passed the initial evaluation in the summer of 2013. 'Above the Clouds' has been asexually propagated by division at the same nursery since 2018 and also by careful shoot tip plant tissue culture with the resultant asexually propagated plants having retained all the same traits as the original plant. *Hosta* 'Above the Clouds' has been stable and reproduced true to type plants in successive generations of asexual reproduction.

There are nearly 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Blue Angel' (not patented), 'Blueberry Muffin' (not patented), 'Diamond Lake' U.S. Plant Pat. No. 30,769, 'Hadspen Blue' (not patented), 'Humpback Whale' (not patented), 'Deep Blue Sea' (not patented) and 'Prairie Sky' U.S. Plant Pat. No. 17,309.

'Silver Moon' is smaller in habit and in foliage size, the flowers have a darker purple stripe in the center of the tepals, and leaves are not as glaucous. The proprietary unnamed sport of 'Liberty' is larger, more upright and has variegated foliage and the leaf color is not as bluish.

'Blue Angel' has a larger habit with taller flower scapes and larger foliage that is more cordate and less rounded and also less glaucous. 'Blueberry Muffin' is more compact and shorter in habit, has a longer, more pointed and more cordate leaf blade and the petiole has more dense reddish stippling. 'Diamond Lake' has larger foliage with more sinuate margins. 'Hadspen Blue' has a smaller habit with smaller leaves that are less bullate to nearly flat and the leaf shape is more ovate. 'Humpback Whale' has a larger habit and larger leaves that are less glaucous. 'Deep Blue Sea' has foliage that is more bullate and the leaf is more concaved. 'Prairie Sky' has leaves that are smaller and more bluish-colored.

Other *Hosta* cultivars may have individual traits similar to 'Above the Clouds' but the new plant differs from the above listed cultivars and all other *Hostas* known to the applicant, by the combination of the following traits.

1. Leaves are medium-sized, nearly round to broadly ovate, with broadly acute apices and cordate base;
2. Arching leaves and petioles produce a tight, medium-sized, mounded habit;
3. Leaves are very glaucous and produce a strongly bluish foliage effect that persists until late in the season;

4. Flowers are white, with light lavender central lines and pale lavender backs;
5. Flowers are densely arranged on scapes with the first flowers beginning to open above the foliage;
6. Floral bracts subtend each flower color with a closely matched color making the whole scape more effective;
7. Useful in the garden as edging or front border, in containers, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings show an eight-year-old 'Above the Clouds' plant in a trial garden at a nursery in Zeeland, Mich. with supplement fertilizer and water as needed.

DETAILED BOTANICAL DESCRIPTION

Figure 1:
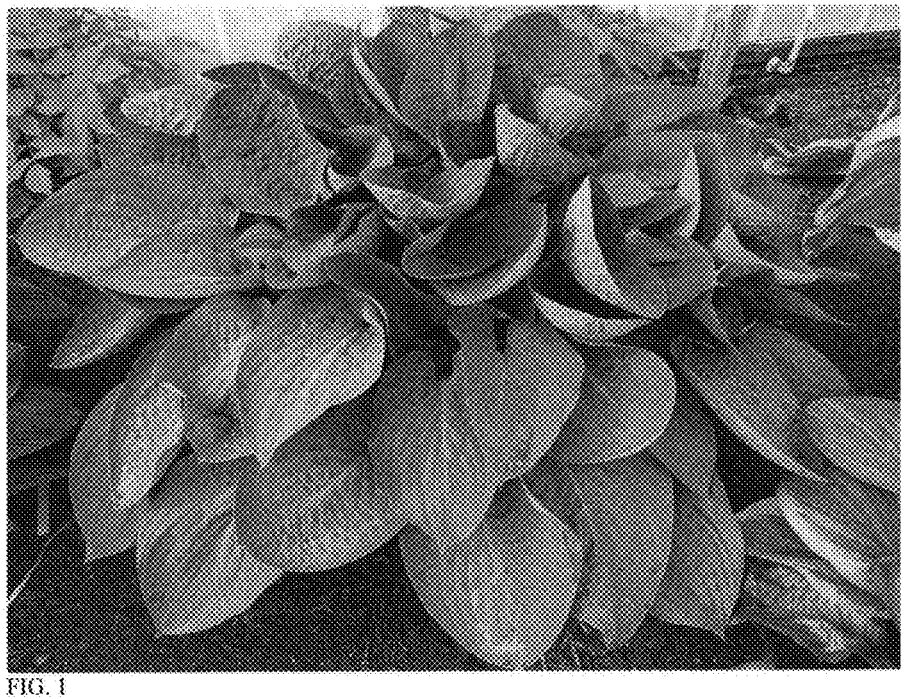
FIG. 1 shows the landscape foliage habit of a new plant prior to flowering.
Figure 2:
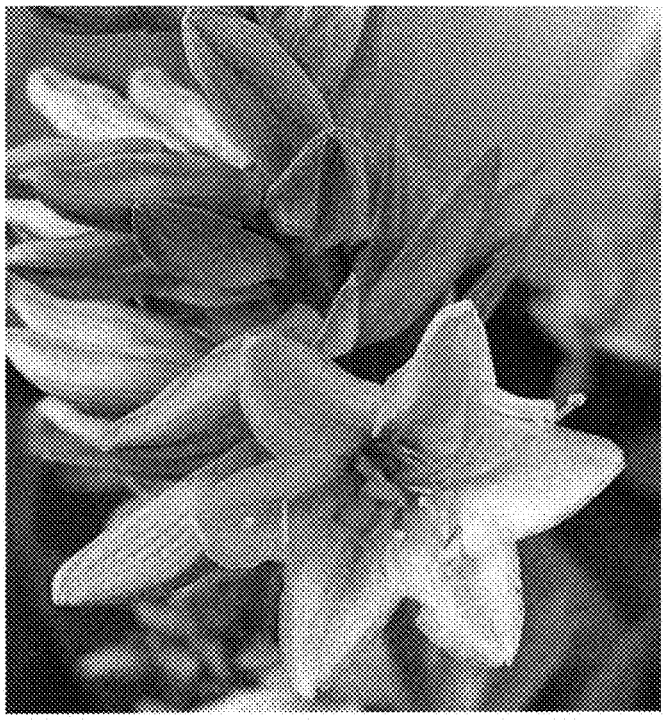
FIG. 2 shows a close-up of the flowers, buds and foliar bracts.
Figure 3:
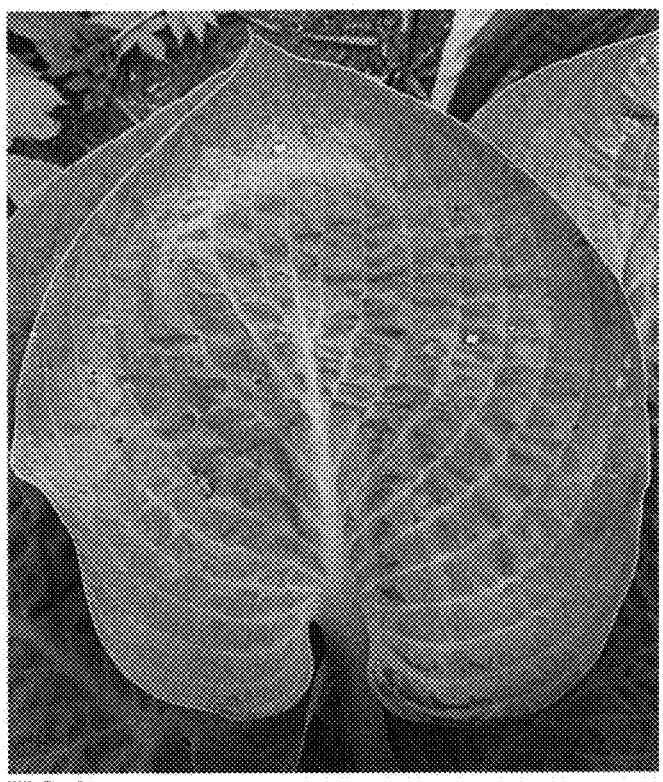
FIG. 3 shows a close-up of a leaf.

The following descriptions and color references are based on the 2015 edition of The Royal Horticultural Society Colour Chart except where common dictionary terms are used. The new plant, *Hosta* 'Above the Clouds', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a eight-year-old plant in a shaded trial garden in Zeeland, Mich. with supplemental water and fertilizer.

Botanical classification: *Hosta* x hybrid;

Parentage: Female or seed parent is 'Silver Moon'; male or pollen parent is a proprietary unnamed sport of 'Liberty';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a medium-sized mound of arching petioles and leaves and erect scapes flowering above foliage;

Plant size: Foliage height to about 63.5 cm above soil line to the top of the leaves, to about 96.5 cm tall to the top of the flowers and to about 149.9 cm wide at the widest point just above the soil line;

Foliage description: Nearly rounded to broadly ovate; broadly acute apex, cordate base; margin entire, slightly cupped to flat; glabrous both surfaces, lightly bullate, and adaxial matte and abaxial highly glaucous until late in the growing season; flexible but stiff; leaf blade profile tends to be slightly cupped only on inner shoot leaves early in the season, and all leaves tend to become flat later in season;

Leaf blade size: To about 27.9 cm long and about 22.9 cm wide about mid-way from the base; average about 24.5 cm long and 21.0 cm wide; not variegated;

Leaf blade color: Early season and expanding adaxial nearest RHS N138A, abaxial nearest RHS 191B; mid-season and mature adaxial between RHS 122A and RHS N138A, abaxial nearest RHS 189B;

Veins: 11 to 12 pairs plus midrib; slightly impressed adaxial and costate and smooth abaxial;

Vein color: Young adaxial nearest RHS N144A, abaxial nearest RHS 147C; mature adaxial nearest RHS 194C and abaxial nearest RHS 191C;

Petiole: Glabrous and moderately glaucous both adaxial and abaxial; deeply concavo-convex proximally and more shallowly concavo-convex distally; stiff; to 36.5 cm long and 22.0 mm wide at base and about 10.0 mm deep near base, average about 33.5 cm long and 20.0 mm wide and 7.0 mm deep at base;

Petiole color: Adaxial between RHS N138D and RHS 189B, abaxial between RHS N138D and RHS 189B with abaxial midrib nearest RHS 145C;

Flower description:

Buds one to two days prior to opening: Clavate with acute apex and narrow tube proximally with base sunken back toward apex at pedicel to produce cordate to auriculate appearance; about 34.0 mm long and 12.0 mm in diameter at the widest portion in the bulb with tube narrowing in basal 6.0 mm to about 5.0 mm diameter;

Bud color: Lighter than RHS 84D distally and tube proximally nearest RHS 84D;

Flowers: Perfect; incomplete; flared campanulate; attitude outwardly; to 39.0 mm long to exserted anthers; corolla fused in basal 13.0 mm, free in the distal 22.0 mm, about 28.0 mm long and 35.0 mm wide at tepal apices, decreasing distally; corolla tube portion 6.0 mm long and 6.0 mm diameter with basal portion indented toward apex up to 9 mm; flowers tightly arranged on scape;

Flowering lasting: Persists for a normal period, usually about one day on plant;

Flowering period: Scapes remain effective with flowers beginning mid-July for about three and a half weeks; with about 46 flowers per scape; mostly secund;

Fragrance: No detectable fragrance;

Tepal: Two nearly identical sets of three identical in size and color, glabrous; entire margins; about 35.0 mm long and 12.0 mm wide slightly above fusion point; fused in basal 13.0 mm; clavate with broadly acute apex;

Tepal color: Adaxial longitudinal center 3.0 mm wide nearest RHS N82D, margin nearest RHS NN155D; abaxial lighter than RHS 84D with indented basal portion nearest RHS 84D; each tepal with a transparent 0.5 mm wide outer margin;

Gynoecium: Variable; irregular length; superior;

*Style*.—Cylindrical; irregularly split either all the way to base, or just near stigma into six or eight stems; about 26.0 mm long, variable diameter from 0.5 mm to 2.0 mm diameter; bent or kinked in irregular fashion; color between RHS 145D and nearest RHS 150D.

*Stigma*.—Puberulent; tri-lobed; variably-sized from 0.7 mm to 2.0 mm across; color between RHS 145D and nearest RHS 150D.

*Ovary*.—Variable; globose to ellipsoidal; superior; apex rounded; base rounded to truncate; size variable, about 5.0 mm long and 5.0 mm diameter in central portion of flower and ovaries around the peripheral portion of the flower about 5.0 mm long and 1.0 mm diameter; color nearest RHS 145A.

Androecium: Variable from flower to flower;

*Filaments*.—Typically one to three partially to fully developed with five to seven vestigial; cylindrical, approximately 33.0 mm long and 1.5 mm in diameter as fully developed and 12.0 mm long and 1.0 mm diameter when vestigial; curved or bent; color distally nearest RHS 158D.

*Anthers*.—Irregular; one to three per flower on average; ellipsoidal with rounded ends; basifixed, longitudinally dehiscent; about 3.5 mm long and 1.5 mm wide when fully developed, others less than 0.5 mm long and 0.5 mm wide; color variable depending on development, nearest RHS 199A to RHS 193B.

*Pollen*.—Rare; spherical; less than 0.1 mm long; color nearest RHS 9B when present.

Peduncle: Cylindrical; usually one per mature division; about 19 per plant; glabrous; highly glaucous; erect; to about 96.5 cm tall, and about 10.0 mm in diameter at base, average about 86.0 cm tall and 8.5 mm diameter at base;

Inflorescence: Flowering portion about 28.0 cm long and 8.0 cm wide; with large lavender blushed floral bracts subtending each flower;

Peduncle color: Proximal portion below leaves nearest RHS 138C and distal portion nearest RHS 138A;

Pedicel: Cylindrical; glabrous; slightly lustrous; to about 18.0 mm long and 2.0 mm diameter, decreasing distally; attitude mostly outwardly;

Pedicel color: Distally nearest RHS 84D, proximally nearest RHS 146D;

Floral bracts: Each flower normally subtended by a single bract; lanceolate; narrowly acute apex and truncate base; entire margin; glabrous and slightly glaucous abaxial and adaxial; to about 42.0 mm long 10.0 mm wide, decreasing distally;

Bract color: At flowering adaxial and abaxial lighter than RHS 84D near longitudinal center with undertone nearest RHS 137C, older bracts after flower drop adaxial and abaxial nearest RHS 161C;

Fruit: No fruit yet observed, but sterility of fecundity unknown;

Seed: Not observed;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature. Hardiness at least from USDA zone 3 through 8, and other disease resistance is typical of that of other *Hostas*.

It is claimed:

1. A new and distinct *Hosta* plant named 'Above the Clouds' as herein described and illustrated.

* * * * *